United States Patent

Randall et al.

[11] 3,951,969
[45] Apr. 20, 1976

[54] N-SUBSTITUTED-P-(2-CHLOROETHYL)-PHOSPHONAMIDATES

[75] Inventors: David I. Randall; Robert W. Wynn, both of Easton, Pa.

[73] Assignee: GAF Corporation, New York, N.Y.

[22] Filed: Feb. 12, 1974

[21] Appl. No.: 441,859

Related U.S. Application Data

[63] Continuation of Ser. No. 875,498, Nov. 10, 1969, abandoned.

[52] U.S. Cl. .................................. 260/247; 71/86; 260/293.51; 260/326.61; 260/958; 260/960
[51] Int. Cl.² ................................ C07D 295/00
[58] Field of Search.......... 260/958, 247.7 L, 297 P, 260/326.5 A, 293.51, 247, 326.61

[56] References Cited
UNITED STATES PATENTS

| | | | |
|---|---|---|---|
| 3,010,986 | 11/1961 | Reetz.................................. | 260/958 |
| 3,626,036 | 12/1971 | Sirrenberg et al............ | 260/247.7 L |
| 3,705,217 | 12/1972 | Vogel.................................. | 260/958 |

OTHER PUBLICATIONS
Popov – C. A. Vol. 42, pp. 7242i–7243.

*Primary Examiner*—Lorraine A. Weinberger
*Assistant Examiner*—P. J. Killos
*Attorney, Agent, or Firm*—Walter C. Kehm

[57] ABSTRACT

Plant growth regulating compounds are N-substituted-P-(2-chloroethyl)-phosphonamidic esters of the formula:

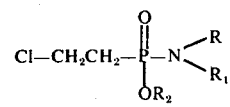

wherein R is cycloalkyl, $R_1$ is hydrogen or cycloalkyl or R and $R_1$ together form a heterocyclic ring such as morpholine, piperidine or pyrrolidine and $R_2$ is alkyl or haloalkyl. They are prepared by the reaction of 2-chloroethylphosphonohalidic esters with the appropriate secondary amine.

6 Claims, No Drawings

N-SUBSTITUTED-P-(2-CHLOROETHYL)-PHOSPHONAMIDATES

This is a continuation of application Ser. No. 875,498, filed Nov. 10, 1969, now abandoned.

BACKGROUND OF THE INVENTION

1. Field of the Invention

This invention relates to N-substituted-P-(2-chloroethyl)-phosphonamidate compounds useful as plant growth regulators and processes for their preparation.

2. Background of the Prior Art

The art is aware that certain phosphorus containing compounds are useful as plant growth regulators. One of the most important phosphorus compounds of this type is 2-chloroethyl-phosphonic acid which has found importance as a plant growth regulator, particularly, in the treatment of pineapples, soy beans and other plants to control their rate of growth. The present invention provides a new class of phosphorus-containing compounds useful as plant growth regulators not known heretofore, which compounds have utility in this area equivalent to 2-chloroethyl phosphonic acid. One of the primary characteristics of products of these types resides in the presence of the 2-chloroethyl group as this is important to the plant growth stimulating activity because it is believed that the action of the compounds is due to the fact that they are absorbed by the plant and release ethylene, a known plant regulator in a form in which it can be used by the plant.

The art is aware of various nitrogen-substituted phosphonamidates but none are suggested as having plant growth activity equivalent to those of the present invention. For example, in *Chemical Abstracts*, Vol. 66, page 27,927, there is disclosed ethyl N,N-diethyl-P-chloromethyl phosphonamidate, which is related to the compounds of the present invention, but the presence of the chloromethyl group negates its value in the plant growth area as the compound cannot release ethylene. In addition, in U.S. Pat. No. 3,010,986, there is disclosed the cyclohexyl ester of N,N-diallyl-P-(2-chloroethyl)-phosphonamidate, prepared by the reaction of 2-chloroethyl phosphonyl dichloride and cyclohexanol followed by the reaction of this intermediate with diallyl amine which compound is obviously different than those claimed herein. Also, in *Chemical Abstracts*, Vol. 42, page 7,243, the compound 2-chloroethyl-N-phenyl-P-(2-chloroethyl) phosphonamidate is suggested as being prepared from its acid chloride and aniline. In none of these prior art teachings however, is there a disclosure of the 2-chloroethyl-N-substituted phosphorus compounds of this invention and in particular, 2-chloroethyl-N-substituted phosphorus compounds which have unique activity as plant growth regulators. Accordingly, there is a clear need in the art for products of this type and processes by which they may be prepared.

SUMMARY OF THE INVENTION

It is accordingly one object of this invention to provide a new class of compounds comprising N-substituted-(2-chloroethyl) phosphonamidates.

A further object of the invention is to provide economical processes by which these products may be produced.

It is a still further object of the invention to provide N-substituted-P-(2-chloroethyl) phosphonamidate esters which may be prepared from readily available materials in an economic manner as well as procedures for their use as plant growth regulators.

Other objects and advantages of the present invention will become apparent as the description thereof proceeds.

In satisfaction of the foregoing objects and advantages, there are provided by this invention plant growth regulators of the following formula:

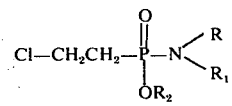

wherein R is cycloalkyl, preferably of about 3-8 carbon atoms, such as cyclopropyl, cyclobutyl, cyclopentyl, cyclohexyl, cycloheptyl and cyclooctyl, $R_1$ is hydrogen or the same as R, or R and $R_1$ together form a heterocyclic ring selected from the group consisting of morpholine, piperidine and pyrrolidine and alkyl substituted derivatives thereof wherein the alkyl group contains 1-5 carbon atoms, and $R_2$ is alkyl of 1-7 carbon atoms, (e.g. methyl, ethyl, propyl, etc.) or haloalkyl of about 1-7 carbon atoms, and preferably, haloalkyl wherein the halogen, which may be chlorine, bromine, iodine or fluorine, but preferably chlorine and preferably disposed on the beta-carbon atom, for example, 2-chloroethyl, 2-chloropropyl, etc.

DESCRIPTION OF PREFERRED EMBODIMENTS

It has been found that the above-identified 2-chloroethyl nitrogen-substituted phosphonamidic esters have unique activity as plant growth regulators and may be applied to plants such as pineapples, soy beans, tomatoes, small grains and the like to regulate growth to thereby improve crop yields thereof. Thus, these compounds may be stated to be plant growth hormones as they operate to increase yields of the products mentioned as well as others.

The compounds of this invention are soluble in varying degrees in water and so they can be applied to the plants in aqueous solutions composed wholly or partially of water; partial solutions include those formed of water and say acetone or methyl ethyl ketone. Any aqueous medium may be used provided that it is not toxic to the plant. Where any particular derivative is less water-soluble, it may be solubilized by the use of co-solvents and the like. Also, the compounds may be adsorbed on solid carriers such as vermiculite, attaclay, talc and the like for application in granular form. Dusts may also be used in which case the active ingredient(s) will be diluted with clays or other powders, for example pyrophyllite, diatomaceous earth and attapulgite.

The compounds of this invention can be applied to the plants at a concentration of from ½ – 10 lbs./Acre or higher, dependent on the particular derivative used. A preferred rate of application ranges from 2 – 5 lbs/Acre. The phosphonic derivatives need only be applied to the plant in low volumes of water to achieve satisfactory initiation, and this is an important advantage of this invention. Whereas it is necessary to apply the known agents in large volumes of water, on the order of 200 – 400 gallons/Acre, even up to 1,000 gallons/Acre in the case of ethylene, to achieve initiation, it is possible to apply a compound of this invention in far lower volumes of water to achieve satisfactory flower initiation. For example, the compounds of the present invention can be applied in 50 gallons of water at the rate of 1 lb./Acre to achieve 100% flower induction on pineapples of the Smooth Cayenne variety. The ability to apply the agent in a reduced volume of water is a great agronomic advantage because a larger acreage of plantation can be treated before recourse to a water supply is necessary, smaller equipment can be used and costs can be reduced generally.

The compounds of this invention may be prepared by the reaction of 2-chloroethyl phosphonohalidic esters of the following formula:

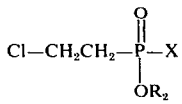

wherein $R_2$ is as above and X is halogen, preferably chlorine, but it may also be bromine, iodine or fluorine, with an amine of the formula:

wherein R and $RR_1$ are as above in the presence of a suitable acid acceptor, the acceptor being employed to remove the hydrogen halide formed during the reaction. The acid acceptor may be provided by use of an excess of the amine or may be provided by utilization of any other acid acceptor well known to the art. Preferred acid acceptors are the tertiary amines such as triethyl amine, trimethyl amine, pyridine, etc., as well as mixtures thereof. Also inorganic acid acceptors may be employed such as alkali metal hydroxides (e.g. NaOH and KOH), alkali metal carbonates ($Na_2CO_3$), bicarbonates ($NaHCO_3$) and the like.

The reaction is conducted in the presence of a solvent which has preferably been dried to remove water prior to use. Preferred solvents to be employed in the process include diethyl ether, dioxane, petroleum ether, aromatic hydrocarbons (e.g. benzene, toluene, etc.), as well as mixtures thereof.

The reaction is conducted at atmospheric pressure and at a low temperature of about −10°C. to 20°C., preferably 0° to 5°C. In addition, in a preferred aspect, each of the reactants are mixed while contained in the solvent. Moreover, the reactants are contacted in stoichiometric quantities.

The process is preferably conducted by charging each of the reacting materials to a portion of the solvent, and the solutions contacted at the low temperatures mentioned. In a preferred procedure, the starting 2-chloroethyl compound is generally charged to a portion of the solvent, cooled to about −10°C to 20°C. and a solution of the amine added thereto. Generally, either an excess of the amine or another acid acceptor is added simultaneously.

After the materials have been mixed, the reaction is generally agitated for a short period at room temperature, the amine salt removed by filtration and the resulting filtrate freed of solvent to provide the products of the invention.

The starting materials in this invention may be prepared in any desired manner but are preferably prepared by the reaction of phosphorus pentahalide with the diester of 2-chloroethyl phosphonic acid of the following formula:

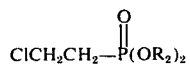

wherein $R_2$ is as above, which then yields the 2-chloroethyl phosphonochloridate of the following formula:

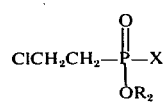

wherein X is as defined above. In this reaction it is of course preferable to use a bis ester in which both of the $R_2$ groups are the same so that only a single 2-chloroethyl phosphonohalidate is formed rather than a mixture thereof.

This reaction is generally conducted by charging the ester of 2-chloroethyl phosphonic acid to a reactor and adding an equivalent amount of the phosphorus pentahalide slowly thereto, preferably portionwise, while maintaining the temperature below about 80°C. Thereafter, after the addition is complete, heating the mixture at reflux for about 2 hours and distilling the resulting product, will provide the intermediate.

In an alternative procedure, the starting materials may be prepared by the reaction of an alcohol of the formula $R_2OH$ wherein $R_2$ is as above, such as absolute ethanol, on 2-chloroethyl phosphonyl dihalide at a temperature of about −10° to 15°C. in the presence of an acid acceptor, such as those mentioned above to provide the intermediate after removal of the salt and solvent.

The following examples are provided to illustrate the compounds and processes of the present invention.

EXAMPLE 1

2-Chloroethyl 2-Chloroethylphosphonochloridate:

There was charged:
889.5 grams (3.3 moles) of

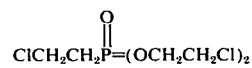

and
686.5 grams (3.3 moles) of phosphorus pentachloride added portionwise while maintaining the temperature below 80°C. The mixture was then refluxed for 2 hours at a pot temperature of 107–109°C. The volatile materials were removed under aspirator vacuum to a final pot temperature of 120°C. The residue was then distilled under vacuum. There was obtained 646.8 g. of product boiling at 105–120°C. at 1 mm pressure. This product was redistilled through a 3.4 × 12 inch Vigreaux head. There was obtained 536.0 grams boiling at 95–104°C. at 0.25-0.30 mm pressure. The product had the structure:

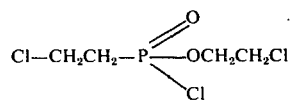

and was used as the starting material for Examples 4 and 5 below.

EXAMPLE 2

Ethyl 2-Chloroethylphosphonochloridate:

There was charged to a reaction flask:
100.8 grams (0.55 mole) of 2-chloroethylphosphonyl dichloride,

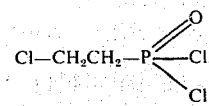

and
500 ml. dry diethyl ether. At a temperature of 0°–5°C. there was added a solution of
23.0 grams (0.5 mole) absolute alcohol in
150 ml. dry ether followed by a solution of
50.5 grams (0.5 mole) triethylamine in
100 ml. dry diethyl ether.

The resulting amine hydrochloride was filtered off and washed with ether. The filtrate was freed from solvent on the flash evaporator and the residue distilled. There was obtained 66.0 grams of product boiling at 45°–48°C. at 0.07–0.09 mm. pressure of the structure

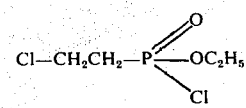

which was used as the starting material for Example 3 below.

EXAMPLE 3

Ethyl 2-Chloroethylphosphonic Morpholide:

A solution of:
19.1 grams (0.1 mol) ethyl 2-chloroethylphosphonochloridate (from Example 2) in
200 ml. dry diethyl ether was cooled to 5°C. and a solution of 8.7 grams (0.1 mol) morpholine and
10.1 grams (0.1 mole) triethylamine in
100 ml. dry diethyl ether added dropwise.

After stirring one hour at room temperature the amine hydrochloride was removed by filtration and washed with ether. The filtrate was freed of solvent by flash evaporation. The residue weighed 22.4 grams.

| Analysis for: | | Calcd. | Found |
|---|---|---|---|
| ClCH₂CH₂P(O)(OC₂H₅)—morpholide | % N | 5.8 | 5.84 |
| | % P | 12.82 | 12.60 |
| C₈H₁₇ClNO₃P | | | |

EXAMPLE 4

2-Chloroethyl N-cyclopropyl-P-(2-chloroethyl) phosphonamidate:

To a solution of:
11.4 grams (0.2 mol) cyclopropylamine and
16.8 grams (0.2 mole) sodium bicarbonate in
95 ml. H₂O in a reaction flask was added
100 cc. diethyl ether. The mixture was cooled to 5°C. and a solution of
45.0 grams (0.2 mole) of 2-chloroethyl 2-chloroethylphosphonochloridate (from Example 1) in
100 ml. diethyl ether added dropwise in 55 minutes.

The mixture was allowed to stir at room temperature overnight. The solution was flash evaporated to dryness. The solid residue was extracted with diethyl ether, and the ether solution filtered. The filtrate was flash evaporated to constant weight to yield a clear, light pink liquid (52.5 grams).

| Analysis: | | Calcd. | Found |
|---|---|---|---|
| ClCH₂CH₂P(O)(OC₂H₄Cl)—N(H)—cyclopropyl | % N | 5.70 | 5.71 |
| | % Cl | 28.90 | 28.93 |
| C₇H₁₄PNO₂Cl₂ | | | |

EXAMPLE 5

2-Chloroethyl 2-Chloroethylphosphonic Morpholide:

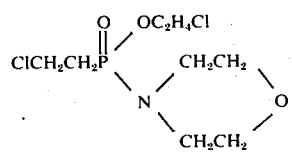

To a solution of:
17.4 grams (0.2 mole) morpholine in
500 ml. dry benzene was added dropwise at 0°–5°C.,
22.5 grams (0.1 mol) 2-chloroethyl 2-chloroethylphosphonochloridate (from Example 1).

After stirring at room temperature for 2 hours the insoluble material was filtered off and the benzene removed from the filtrate on the flash evaporator. The residue weighed 27.3 grams.

EXAMPLE 6

Ethyl 2-Chloroethylphosphonic Piperidide:

The reaction of Example 3 was repeated except that 0.1 mole of piperidide was employed in place of the morpholine. From this reaction, there was recovered 16.2 grams of a compound of the following formula:

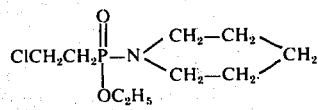

EXAMPLE 7

2-Chloroethyl N-Cyclohexyl-P-(2-Chloroethyl) phosphonamidate:

The reaction of Example 4 was repeated except that 0.2 mole of cyclohexylamine was used in place of the cyclopropylamine. From this reaction, there was recovered 54.6 grams of a compound of the following formula:

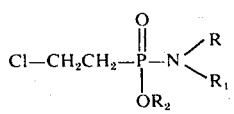

The reaction has been described herein with reference to certain preferred embodiments. However, the invention is not to be considered as limited thereto.

What is claimed is:

1. A compound of the formula:

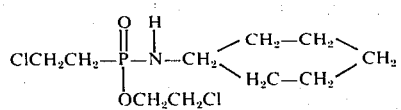

wherein R is cycloalkyl of 3 to 8 carbon atoms, $R_1$ is cycloalkyl of 3 to 8 carbon atoms or hydrogen or R and $R_1$ together with the depicted nitrogen form a heterocyclic ring selected from the group consisting of morpholine, piperidine and pyrrolidine and alkyl substituted derivatives thereof wherein the alkyl group contains 1 to 5 carbon atoms, and $R_2$ is alkyl of 1 to 7 carbon atoms or beta-chloroalkyl of 2 to 7 carbon atoms.

2. A compound according to claim 1 wherein R and $R_1$ together with the depicted nitrogen atom form a morpholine ring and $R_2$ is ethyl.

3. A compound according to claim 1 wherein R is cyclopropyl, $R_1$ is hydrogen and $R_2$ is 2-chloroethyl.

4. A compound according to claim 1 wherein R and $R_1$ together with the depicted nitrogen atom are morpholine and $R_2$ is 2-chloroethyl.

5. A compound according to claim 1 wherein R is cyclohexyl, $R_1$ is hydrogen and $R_2$ is 2-chloroethyl.

6. A compound according to claim 1 wherein R is cyclopentyl, $R_1$ is hydrogen and $R_2$ is 2-chloroethyl.

* * * * *